United States Patent [19]

Briggs et al.

[11] Patent Number: 4,981,679

[45] Date of Patent: Jan. 1, 1991

[54] METHOD AND COMPOSITION FOR THE TREATMENT OF BURNS

[76] Inventors: Joseph H. Briggs, The Roost, Abbott's Well Road, Frogham, Hampshirt; Stanley B. Turner, Lithend House, Free Street, Bishops Waltham, Hampshire, both of United Kingdom

[21] Appl. No.: 250,258

[22] Filed: Sep. 27, 1988

Related U.S. Application Data

[63] Continuation-in-part of Ser. No. 145,698, Jan. 15, 1988, abandoned, which is a continuation of Ser. No. 756,493, filed as PCT GB84/00198 on Jun. 7, 1984, published as WO84/04833 on Dec. 20, 1984, abandoned.

[30] Foreign Application Priority Data

Jun. 8, 1983 [GB] United Kingdom ................. 8315787

[51] Int. Cl.$^5$ ................................................. A61K 9/14
[52] U.S. Cl. ....................................... 424/45; 514/945
[58] Field of Search ............................ 424/45; 222/95

[56] References Cited

U.S. PATENT DOCUMENTS 3,079,299 2/1963 Helig ..................................... 424/45

OTHER PUBLICATIONS

Chemical Abstracts 86: 195161j (1977), Livet.
Chemical Abstracts 92: 648054 (1980), Daimon.

*Primary Examiner*—Douglas W. Robinson
*Assistant Examiner*—Zohyeh A. Fay
*Attorney, Agent, or Firm*—Cushman, Darby & Cushman

[57] ABSTRACT

A method of treating a burn injury comprises administering to the injury a composition comprising petroleum wax, paraffin oil and a topically acceptable refrigerant, wherein subsequent evaporation of the refrigerant is effective to form a foam and maintain the foam at a temperature of from 0° to 10° C. for at least 1 minute. A suitable composition for use in the method comprises an intimate mixture of (a) petroleum wax in an amount of from 3 to 8% by weight of the composition, from 15 to 60% by weight of said wax being in microcrystalline form,
(b) paraffin oil in an amount of from 6 to 15% by weight of the composition, and
(c) the topically acceptable refrigerant or mixture of refrigerants.

13 Claims, No Drawings

METHOD AND COMPOSITION FOR THE TREATMENT OF BURNS

This application is a continuation in part of U.S. patent application Ser. No. 07,145,698 which is a continuation of U.S. patent application Ser. No. 06,756,493 filed as PCT GB84/00198 on Jun. 7, 1984 published as WO84/04883 on Dec. 20, 1984, now both abandoned.

This application is a continuation-in-part of our copending U.S. patent application Ser. No. 145,698, filed Jan. 15, 1988, which is a continuation of our U.S. patent application Ser. No. 756,493, filed July 1, 1985, now abandoned.

This invention relates to a method and composition suitable for use in the emergency treatment of burns, and also for the treatment of other soft tissue injuries, such as bruises or strains of muscles, ligaments and tendons.

It is well known that both pain and tissue damage (and, in particular, oedema) at a burn site can be substantially reduced if the burn site is cooled rapidly to a temperature which is below 30° C., and then maintained at that temperature for a substantial period of time. For example, it is suggested in an article by J. W. L. Davies in Burns, Vol. 9 (1982) pages 1 to 6, that burns should preferably be cooled in water at 20° to 25° C. for an hour or more. The selection of this temperature range is said to avoid the potential hazards of frostbite or hypothermia induced by temperatures near 0° C.

It is also known that pain and tissue damage in the case of bruises, sprains and the like can be reduced by cooling the site of the injury. For example, it has been proposed in Japanese Patent Specification No. 54-86606 to provide cooling in such cases by means of a coolant aerosol comprising one or more organic chemical compounds with a molecular weight greater than 80, a latent heat of evaporation of 100 cal/g or less at 25° C. and a boiling point of 20 to 100° C., together with a compressed gas as a propellant. Such an aerosol is said to provide rapid cooling down to −20° C. or −30° C. at 5 cm from the spray nozzle, and −10° C. to −25° C. at 10 cm from the spray nozzle. Refrigerants such as R12 (dichlorodifluoromethane), which have a boiling point below 20° C., are said to be unsatisfactory by reason of providing only slight cooling of the object which is being sprayed, despite considerable cooling around the nozzle of the aerosol.

The aerosol of Japanese Patent Specification No. 54-86606 suffers from the disadvantage that it is difficult to obtain a cooling effect which is of sufficient duration to give optimal pain relief and minimum tissue damage. A relatively long cooling effect is only obtained by choosing refrigerants which yield very low temperatures such as the temperatures mentioned above. This involves the risk of frostbite or hypothermia, especially to patients who are in a state of shock, such as burns patients. The aerosol disclosed in Japanese Patent Specification No. 54-86606 is therefore believed to be wholly unsuitable for the emergency treatment of burns.

U.S. Patent Specification No. 3079299 (Heilig) discloses a self-propelling fluid medical ointment composition adapted to be atomized from a fluid-tight container and which, when applied directly as a fine spray or mist on the body to be treated, is of such a character as to provide a breathing covering of polyethylene filaments from which the medicant is rapidly released to the treated area of the body. The composition is said to be effective in the treatment of burns.

The gaseous propellants used in the compositions of the Heilig patent are said to vaporise almost instantly as the spray leaves the distributor valve of the dispenser. Although this may be of advantage in producing a breathing film which permits access of air and oxygen to the affected area of the body and facilitates the rapid release of the medicant to the affected area, it means that the compositions of the Heilig patent are not able to provide the prolonged cooling which, if applied within the first few minutes after a burn injury is sustained, is effective to reduce tissue damage. A further disadvantage of the rapid loss of propellant from the compositions disclosed in the Heilig patent is that the solid material of the composition leaves the dispenser nozzle at relatively high velocities, carrying the risk that particles of the composition striking the wound will penetrate the wound and cause further damage.

According to the present invention, there is provided a refrigerant composition suitable for the emergency treatment of burns, comprising an intimate mixture of
  (a) petroleum wax in an amount of from 3 to 8% by weight of the composition, from 15 to 60% by weight of said wax being a microcrystalline wax,
  (b) paraffin oil in an amount of from 6 to 15% by weight of the composition, and
  (c) a topicallY acceptable refrigerant or mixture of refrigerants.

Petroleum waxes are conventionally classified as paraffin waxes, intermediates and microcrystalline waxes. Paraffin waxes are mixtures of alkanes, generally having a chain length of from about 18 to about 45 carbon atoms. Straight-chain alkanes constitute the major component but some smaller quantities of branched-chain alkanes are also present, together with some cycloalkanes. The high proportion of straight-chain molecules in paraffin waxes leads to their ready crystallization Intermediate waxes are similar to paraffin waxes, but include higher molecular weight molecules (alkanes having up to about 60 carbon atoms), and generally a higher proportion of branched-chain components, though still less than about 50% of the whole.

Microcrystalline waxes are also mixtures of saturated alkanes, but branched-chain and cycloalkanes are preponderant, with chain lengths varying from between about 30 or 35 to 80 or more carbon atoms. The complex branched-chain structure interferes with close packing of the molecules and prevents macrocrystallization.

Paraffin waxes may have a viscosity in the range 2 to 5 Cst at 100° C., as determined according to ASTM D445. In contrast, a microcrystalline wax may have a viscosity of from 10 to 20 Cst under the same conditions.

Paraffin waxes are generally softer than microcrystalline waxes, and this is demonstrated by the needle penetration values as determined by ASTM D1321. The needle penetration of a petroleum wax is the distance in units of 0.1 mm to which a standard needle penetrates into the sample under particular conditions of load, time and temperature. Typical values for paraffin waxes at 25° C. are from 25 to 50, while typical values for microcrystalline waxes are from 10 to 35.

As would be expected from the generally higher molecular weights of microcrystalline waxes, such waxes show a higher congealing point than do paraffin waxes. The congealing point may be determined according to ASTM D938 by applying a drop of molten wax to a thermometer bulb, and noting the temperature at which the wax congeals when the thermometer is rotated under standard cooling conditions. The congealing point of a typical paraffin wax is between 45° and 55° C., while microcrystalline waxes typically have congealing points in excess of 57° C., e.g. from 60° to 70° C.

A suitable paraffin wax for use in the compositions of the present invention is available from Astor Chemical Limited under the Trade Mark Okerin 48. This wax has a congealing point between 48 and 51° C., a needle penetration at 25° C. between 28 and 40 and a viscosity at 100° C. between 3 and 3.5 Cst.

A suitable microcrystalline wax for use in the compositions of the present invention is also available from Astor Chemical Limited, under the Trade Mark Okerin 140. This wax has a congealing point between 63° and 66° C., a needle penetration at 25° C. between 20 and 30 and a viscosity at 100° C. between 15 and 17.

The composition is suitably delivered to the site of an injury from a conventional aerosol dispenser. When sprayed in this way, the composition generates a foam or mousse, from which refrigerant is gradually lost over a period of up to several minutes, thus providing prolonged cooling to the injury to which it is applied.

Moreover, the incorporation of a relatively high proportion of refrigerant in the composition as it leaves the dispenser nozzle means that the velocity with which it leaves the nozzle is greatly reduced, thus virtually eliminating the danger of further damage to the injury site.

The microcrystalline wax provides adhesion to the skin surface in the early stages of spraying, and prevents the first layer of the refrigerant composition from being dislodged from the skin by the force of the spray. However, if too high a proportion of microcrystalline wax is used, the degree of adhesion may be too great, and difficulty may be experienced in removing the wax from the site of injury after treatment.

Preferably, the microcrystalline wax constitutes from 25 to 45% by weight of the paraffin wax, and more preferably from 30 to 40% by weight.

If the proportion of wax as a whole in the composition is too high, it is found that difficulties are encountered in forming a stable, uniform dispersion thereof in the refrigerants. However, if the proportion of wax is too low, the foam itself may be insufficiently stable, and refrigerant may be lost too quickly, resulting in rapid but relatively brief cooling. Particularly satisfactory results are obtained if the amount of petroleum wax (including microcrystalline wax) in the composition constitutes from 3 to 7% by weight, more preferably 4 to 6%, e.g. from 4.5 to 5.5% by weight.

The paraffin oil or liquid paraffin provides plasticity in the early stages of spraying, and also assists in removal of the product after treatment. The paraffin oil is advantageously present in an amount of from 8 to 12% by weight of the composition, and most preferably 9 to 10% by weight.

The refrigerant or mixture of refrigerants is chosen such that on spraying the composition onto skin at a range of about 1 inch to 12 inches, e.g. from 2 to 6 inches, a foam or mousse having an initial temperature of from 0° to 10° C. is obtained. Preferably, the initial temperature is from 0° to 5° C. These temperatures are sufficiently low to produce substantial anaesthesia (because the nerves which are responsible for signalling pain are not effective at temperatures below about 5° C.), but the temperatures are not so low as to present any danger of frostbite or hypothermia.

Accordingly, the present invention also provides a method of treating a burn injury, comprising administering to said injury a composition comprising paraffin wax, paraffin oil and a topically acceptable refrigerant, wherein subsequent evaporation of said refrigerant is effective to maintain said composition at a temperature of from 0° C. to 10° C. for at least 1 minute.

Preferably, the temperature of said composition remains below 10° C. for at least 1.5 minute, and more preferably at least 2 minutes. In a particularly preferred embodiment, the temperature of the composition remains below 10° C. for at least 4 minutes.

In order to minimise pain felt by the patient, the composition preferably remains at a temperature below 8° C., and more preferably between 0.5° C. and 5° C. for at least 30 seconds. Particularly effective are compositions which maintain a temperature below 8° C. (e.g. 0.5° C. to 5° C.) for at least 1 minute, and preferably at least 2 minutes.

The refrigerant used in the composition and method of the invention preferably comprises one or more halogenated hydrocarbons. Particularly preferred are fluorinated hydrocarbons.

If a single refrigerant is to be used, it should preferably have a boiling point below 10° C. It is greatly preferred, however, that two or more refrigerants be used, each having different boiling points. This has the advantage that rapid evaporation of the lower boiling component generates the foam and produces the initial cooling effect, while subsequent slower evaporation of the higher boiling component or components serves to keep the foam at its low temperature. Thus, for example, the refrigerant may be comprise a component having a boiling point in the range −60° C. to 10° C., and more preferably in the range −40° C. to −20° C., and a component having a boiling point in the range 10° C. to 40° C., for example 20° C. to 30° C. In particularly preferred embodiments, three refrigerants are used, namely a low boiling component having a boiling point in the range −40° C. to −20° C., for example −30° C., a high boiling component having a boiling point in the range 10° C. to 40° C., for example 24° C., and an intermediate boiling component having a boiling point in the range 20° C. to 10° C., for example 4° C.

The use of an intermediate boiling component allows the proportion of higher boiling component to be reduced without sacrificing (and even improving) the long term cooling properties. This avoids a difficulty which can arise if too high a proportion of the higher boiling component is used, namely that the composition may become quite mobile after loss of the lower boiling component, thus reducing the efficiency of treatment and running the risk of soiling the patient's clothing.

When just two refrigerants are used, the lower boiling component is preferably present in an amount of from 40 to 80% by weight of the composition, and more preferably from 50 to 70% by weight, for example 60% by weight. The higher boiling component is advantageously present in an amount of from 20 to 40% by weight of the composition, and preferably from 25 to 30% by weight, for example 30% by weight.

When three refrigerants are used, the lowest boiling component is advantageously present in an amount of from 30 to 50% by weight of the composition, and preferably in an amount of from 25 to 40% by weight, for example 30 to 35% by weight. The high boiling component is preferably present in an amount of from 8 to 24% by weight of the composition, and more preferably in an amount of from 10 to 18% by weight, for example from 12 to 14% by weight. The intermediate boiling component is preferably present in an amount of from 25 to 50% by weight of the composition, and more preferably from 30 to 45% by weight, for example, 38 to 42% by weight.

The refrigerant (or the lowest boiling component thereof if a mixture of refrigerants is used) preferably has a latent heat of evaporation of at least 5000 kJ/mole, and more preferably at least 8000 kJ/mole, for example 9000 kJ/mole.

Preferred refrigerants are dichlorodifluoromethane (R12), which has a boiling point of −29.8° C., trichloromonofluoromethane (R11), which has a boiling point of 23.8° C., and dichlorotetrafluoroethane (R114), which has a boiling point of 4.1° C.

The refrigerant can be used as the propellant for dispensing the composition from a container. That is to say, it is not necessary to use a compressed gas such as carbon dioxide or nitrogen, because the refrigerant has a sufficiently high vapour pressure at room temperature to drive the mixture of refrigerant and foam-forming material from the container. While a compressed gas may be used if desired, its use has the disadvantage of adding expense, and also means that pressure is steadily lost from the dispenser during use.

The container which is used for the composition of the present invention may be filled in any conventional way. If a relatively high proportion of a high boiling refrigerant is used, it is convenient to dissolve the wax and paraffin oil in such high boiling refrigerant, and to fill the container with this solution at or around ambient temperature (e.g. about 20° C.). On the other hand, if a relatively low proportion of high boiling refrigerant is used, the wax and oil may not be fully soluble in the high boiling refrigerant, and it is then convenient to fill the container with a mixture of the wax and oil at an elevated temperature, such as from 40° C. to 80° C., and preferably at a temperature of from 45° C. to 60° C., e.g. about 50° C. The lower boiling refrigerants are then added to the container in a subsequent step, preferably at ambient temperature or below ambient temperature.

The composition of the present invention may contain other additives, such as antibacterial agents. A mixture of such agents may be used to achieve a broad spectrum of antibacterial activity. An example of such a mixture is a mixture of neomycin sulphate, polymyxin sulphate and bacitracin zinc.

For certain applications, it may also be desirable to incorporate a local anaesthetic in the refrigerant foam. When the foam is to be used in the emergency treatment of burns, however, it is advisable to avoid the incorporation of an anaesthetic, because pain at a burn site is a useful indication that insufficient cooling has been achieved.

If additives other than the petroleum wax, paraffin oil and refrigerant are included in the composition, they will generally be present in an amount less than 10% by weight, preferably less than 5% by weight, and most preferably less than 2% by weight.

The invention is further illustrated by the following Examples.

| Example 1 |  |
|---|---|
| A conventional aerosol canister was filled with the following composition: |  |
|  | % w/w |
| Microcrystalline wax (Okerin 140) | 1.75 |
| Paraffin wax (Okerin 48) | 3.25 |
| Paraffin oil | 10.00 |
| Refrigerant R11 | 45.00 |
| Refrigerant R12 | 40.00 |
|  | 100.00 |

When sprayed onto skin from a distance of approximately 3 inches (75 mm), yielded a foam which built up to a depth of approximately 4 mm in 5 seconds. This foam reduced the skin temperature to below 14° C. for about 2 minutes.

| Comparative Example 1 |  |
|---|---|
| Example 1 was repeated with the following composition: |  |
|  | % w/w |
| Paraffin Wax (Okerin 48) | 5.00 |
| Paraffin oil | 10.00 |
| Refrigerant R11 | 45.00 |
| Refrigerant R12 | 40.00 |
|  | 100.00 |

This composition had very little adhesion to skin, with the result that it was difficult to build up a substantial quantity of foam on the site to which it was applied. However, once applied to a satisfactory depth (about 4 mm), it was found to give comparable cooling to the composition of Example 1.

| Example 2 |  |
|---|---|
| Example 1 was repeated with the following composition: |  |
|  | % w/w |
| Microcrystalline wax (Okerin 140) | 1.75 |
| Paraffin wax (Okerin 40) | 3.25 |
| Paraffin oil | 10.00 |
| Refrigerant R11 | 22.00 |
| Refrigerant R12 | 40.00 |
| Refrigerant R114 | 23.00 |
|  | 100.00 |

This composition was found to maintain skin temperature below 8° C. for about 20 seconds, and to provide cooling for several minutes at a somewhat higher temperature.

| EXAMPLE 3 |  |
|---|---|
|  | % w/w |
| Microcrystalline wax (Okerin 140) | 1.40 |
| Paraffin wax (Okerin 48) | 2.60 |
| Paraffin oil | 8.00 |
| Refrigerant R11 | 13.00 |
| Refrigerant R12 | 37.00 |
| Refrigerant R114 | 38.00 |
|  | 100.00 |

This compositions with a somewhat lower proportion of waxes than the composition of Examples 1 and 2, was rather mobile after application, but nonetheless gave a very useful degree of cooling. Continuous monitoring with a type J thermocouple feeding into a Comark microprocessor thermometer revealed that the temperature fell rapidly to 10° C. immediately after spraying and then more slowly to 8° C. It remained at this level for about 1 minute and then rose quickly to 14° C. and less quickly back to 27° C.

EXAMPLE 4

Example 1 was repeated with the following composition:

| | % w/w |
|---|---|
| Microcrystalline wax (Okerin 140) | 1.75 |
| Paraffin wax (Okerin 48) | 3.25 |
| Paraffin oil | 10.00 |
| Refrigerant R11 | 13.00 |
| Refrigerant R12 | 37.00 |
| Refrigerant R114 | 35.00 |
| | 100.00 |

This composition gave rapid cooling down to 8° C. and maintained this temperature for approximately 1.5 minutes, after which time the temperature slowly rose again.

EXAMPLE 5

Example 1 was repeated with the following composition:

| | % w/w |
|---|---|
| Microcrystalline wax (Okerin 140) | 1.75 |
| Paraffin wax (Okerin 48) | 3.25 |
| Paraffin oil | 10.00 |
| Refrigerant R11 | 13.00 |
| Refrigerant R12 | 34.00 |
| Refrigerant R114 | 38.00 |
| | 100.00 |

This composition gave very rapid cooling to about 0° C., and a temperature below 8° C. was maintained for over 2 minutes.

EXAMPLE 6

Example 1 was repeated with the following composition:

| | % w/w |
|---|---|
| Microcrystalline wax (Okerin 140) | 1.75 |
| Paraffin wax (Okerin 48) | 3.25 |
| Paraffin oil | 10.00 |
| Refrigerant R11 | 13.00 |
| Refrigerant R12 | 32.00 |
| Refrigerant R114 | 40.00 |
| | 100.00 |

After spraying, this composition gave rapid cooling of skin down to about 8° C. The temperature then fell further over the next 20 seconds to below 4 degrees, and not exceed that level again until after a further 1.5 minutes had elapsed.

Comparison of these results with the results obtained in Example 2 illustrates the advantageous effect of using a comparatively high proportion (from 38 to 42% w/w) of Refrigerant R114.

It will be appreciated that the present invention has been described above by way of example only, and many variations are possible within the scope of the invention.

We claim:

1. A foam-forming refrigerant composition suitable for the emergency treatment of burns, comprising an intimate mixture of:
    (a) petroleum wax in an amount of from 3 to 8% by weight of the composition, from 15 to 60% by weight of said wax being a microcrystalline wax,
    (b) paraffin oil in an amount of from 6 to 15% by weight of the composition, and
    (c) a topically acceptable refrigerant or mixture of refrigerants, said refrigerant or refrigerants being provided at least for the cooling properties thereof so as to cool the tissue to which the composition is applied;
    whereby a composition is provided having sufficient adhesion to prevent to first layer of the same from being dislodged from the tissue during application while allowing removal from the tissue after treatment and whereby the tissue to which is sufficiently low to produce substantially anesthesia for at least 1 minute without that generating frostbite or hypothermia.

2. A composition according to claim 1 wherein the microcrystalline wax constitutes from 25 to 45% by weight of the petroleum wax.

3. A composition according to claim 1 wherein the microcrystalline wax constitutes from 30 to 40% by weight of the petroleum wax.

4. A composition according to claim 1 wherein the total amount of petroleum wax constitutes from 3 to 7% by 5. A composition according to claim 1 wherein the total amount of petroleum wax constitutes from 4 to 6% by weight of the composition.

6. A composition according to claim 1 wherein the paraffin oil is present in an amount of from 8 to 12% by weight of the composition.

7. A composition according to claim 1 wherein the refrigerant is a mixture of dichlorodifluoromethane, trichloromonofluoromethane and dichlorotetrafluoroethane.

8. A composition according to claim 1 comprising dichlorodifluoromethane in an amount of from 30 to 50% by weight of the composition, trichloromonofluoromethane in an amount of from 8 to 24% by weight of the composition and dichlorotetrafluoroethane in an amount of from 25 to 50% by weight of the composition.

9. A composition according to claim 1 wherein the refrigerant comprises dichlorodifluoromethane in an amount of from 25 to 40% by weight of the composition, trichloromonofluoromethane in an amount of from 10 to 18% by weight of the composition, and dichlorotetrafluoroethane in an amount of from 30 to 45% by weight of the composition.

10. A method of treating a burn injury, comprising administering to said injury a foam-forming composition comprising:
    (a) petroleum wax in an amount of from 3 to 8% by weight of the composition, from 15 to 60% by weight of said wax being a microcrystalline wax,
    (b) paraffin oil in an amount of from 6 to 15% by weight of the composition, and
    (c) a topically acceptable refrigerant, said refrigerant being provided at least for the cooling properties thereof so as to cool the tissue to which the composition is applied,
    wherein administration forms a foam and subsequent evaporation of said refrigerant is effective to maintain said foam at a temperature of from 0° to 10° C. for at least 1 minute.

11. A method according to claim 10 wherein the temperature of said foam remains below 10° C. for at least 1.5 minutes.

12. A method according to claim 10 wherein the temperature of said foam remains blow 8° C. for at least 1 minute and below 10° C. for at least 2 minutes.

13. A method according to claim 10 wherein the temperature of said foam remains between 0.5° and 5° C. for at least 1 minute, below 8° C. for at least 1.5 minutes, and below 10° C. for at least 4 minutes.

* * * * *